(12) United States Patent
Carillo et al.

(10) Patent No.: US 7,837,991 B2
(45) Date of Patent: Nov. 23, 2010

(54) METHOD OF CANCER TREATMENT BY P53 PROTEIN CONTROL

(75) Inventors: Serge Carillo, Nimes (FR); Jean-Marie Blanchard, Castelnau-le-Lez (FR); Marc Piechaczyk, Saint Gely du Fesc (FR)

(73) Assignee: Aventis Pharma, S.A., Antony (FR)

( * ) Notice: Subject to any disclaimer, the term of this patent is extended or adjusted under 35 U.S.C. 154(b) by 1477 days.

(21) Appl. No.: 10/788,489

(22) Filed: Mar. 1, 2004

(65) Prior Publication Data

US 2007/0184042 A1 Aug. 9, 2007

Related U.S. Application Data

(60) Division of application No. 09/405,920, filed on Sep. 24, 1999, now abandoned, which is a continuation of application No. 08/737,953, filed as application No. PCT/FR95/00670 on May 22, 1995, now abandoned.

(30) Foreign Application Priority Data

May 31, 1994 (FR) .................................. 94 06583

(51) Int. Cl.
G01N 33/574 (2006.01)
A61K 38/55 (2006.01)
(52) U.S. Cl. .................................. 424/94.2; 435/7.23
(58) Field of Classification Search ........................ None
See application file for complete search history.

(56) References Cited

U.S. PATENT DOCUMENTS

| 4,788,219 | A |   | 11/1988 | Sakurai et al. | 514/523 |
| 5,496,731 | A | * | 3/1996 | Xu et al. | 435/320.1 |
| 5,607,831 | A | * | 3/1997 | Henkart et al. | 435/5 |
| 5,629,165 | A | * | 5/1997 | Nixon et al. | 435/7.21 |

FOREIGN PATENT DOCUMENTS

| EP | 159 678 | 10/1985 |
| EP | 395 309 | 10/1990 |
| EP | 569 122 | 11/1993 |
| EP | 569122 | 11/1993 |
| EP | 580 161 | 1/1994 |
| WO | 92/21373 | * 12/1992 |
| WO | WO 92/21373 | 12/1992 |
| WO | WO/92/21373 | 12/1992 |
| WO | WO93/02106 | 2/1993 |
| WO | WO 93/02106 | 2/1993 |
| WO | WO 94/21817 | 9/1994 |
| WO | WO 00/21575 | 4/2000 |

OTHER PUBLICATIONS

Asada et al. J. Enzym. Inhib. 3 (1), 49-56 (1989).*
Rambsy et al. Electrophoresis. Feb. 1994;15(2):265-77.*
Carafoli et al. (Biochemical and Biophysical Research Communications, 1998; 247: 193-203).*
Squier et al. (Journal of Cellular Physiology, May 1994; 159(2): 229-237).*
Maki et al. (The Journal of Biological Chemistry, Nov.15, 1989; 264(32): 18866-18869).*
Haake et al. (J Invest Dermatol, 1993; 101: 107-112).*
Lowe et al. (Nature. Apr. 29, 1993; 362: 847-849).*
Robaye et al. (Electrophoresis. 1994; 15: 503-510).*
Lane et al (British Medical Bulletin. 1994; 50(3):582-599).*
Huibregtse et al. (Molecular and Cellular Biology. Aug. 1993; 13(8): 4918-4927).*
Huibregtse et al. (EMBO Journal. 1991; 10(13): 4129-4135).*
Marshall; Gene Therapy's Growing Pains, 1995, Science, vol. 269: 1050-1055.*
Asada et al., "cDNA cloning of human calpastatin: sequence homology among human, pig, and rabbit calpastatins." J. Enzym. Inhib., vol. 3 (1): 49-56, 1989.*
Bischoff et al., "An adenovirus mutant that replicates selectively in p53-deficient human tumor cells." Science, vol. 274 : 373-376, Oct. 1996.*
Miller et al., "Targeted vectors for gene therapy." FASEB, vol. 9: 190-199, Feb. 1995.*
Crystal, RG., "Transfer of Genes to Humans: Early lessons and obstacles to success." Science, vol. 270: 404-410, 1995.*
Dach et al., "Targeting gene therapy to cancer: a review." Oncology Res., vol. 9: 313-325, 1997.*
Verma et al., "Gene therapy—promises, problems and prospects." Nature, vol. 389: 239-242, Sep. 1997.*
Deonarain, MP., "Ligand-targeted receptor-mediated vectors for gene delivery." Exp. Opin. Ther. Patents, vol. 8 (1): 53-69, 1998.*
Eck et al., "Gene-based therapy." Goodman & Gilman's The Pharmacological Basis of Therapeutics, McGraw-Hill-Nith Edition: 77-101, 1996.*
Orkin et al., "Report and recommendations of the panel to assess the NIH investment in research on gene therapy." pp. 1-20, Dec. 1995.*
Orkin et al (1995) Report and Recommendation of the Panel to Access the NIH Investment in Research on Gene Therapy.*
Y Emori et al (1988) J Biol Chem 263: 2364-2370.*
H Witschi et al (1989) Carcinogenesis 10: 2275-2277.*
W Troll et al (1984) JNCI.73: 1245-1250.*
M Ohkoshi (1980) Gann 71: 246-250.*
Levrero etal (1991) Gene 101: 195-202.*
Maki etal (1989) J. Biol. Chem 264: 18866-18869.*
Anderson, W. French, Nature Medicine, vol. 6, No. 8, p. 862 (Aug. 2000).
Wagenknecht et al., "Proteasome Inhibitors Induce p53/p21-Independent Apoptosis in Human Glioma Cells", Cell Physiol Biochem 1999; 9:117-125.

(Continued)

Primary Examiner—Scott Long
(74) Attorney, Agent, or Firm—Wiley Rein LLP (57) ABSTRACT

Method of cancer treatment by controlling cellular p53 protein levels. The invention concerns, in particular, the use of a compound capable of modulating calpaine activity.

6 Claims, 1 Drawing Sheet

OTHER PUBLICATIONS

An et al., "Protease inhibitor-induced apoptosis: accumulation of wt p53, p51 WAF1/CIP1,and induction of apoptosis are independent markers of proteasome inhibition", Leukemia (2000) 14; 1276-1283.

Kubbutat et al., "Proteolytic Cleavage of Human p53 by Calpain: a Potential Regulator of Protein Stability", Molecular and Cellular Biology, Jan. 1997; pp. 460-468.

Kubbutat and Vousden, "Keeping an old friend under control: regulation of p53 stability", Molecular Medicine Today, Jun. 1998; pp. 250-256.

Atencio et al., "Celpain Inhibitor 1 Activates p53-dependent Apoptosis in Tumor Cell Lines", Cell Growth & Differentiation, May 2000; vol. 11, 247-253.

Pariat, et al., "Proteolysis by Calpains: a Possible Contribution to Degradation of p53", Milecular and Cellular Biology, May 1997; vol. 17 No. 5, pp. 2806-2815.

Carafoli, et al., "Breakthrough and Views Calpain: A Protease in Search of a Function?", Biochemical and Biophysical Research Communications 247, 193-203 (1998).

Levrero et al., Defective and Nondefective Adenovirus Vectors for Expressing Foreign Genes In Vitro and In Vivo, Gene, 101, 195-202, (1991).

Maki et al., Inhibition of Calpain by a Synthetic Oligopeptide Corresponding to an Exon of the Human Calpastatin Gene, Journal of Biol. Chemistry, 264, (32), 18866-18869, (1989).

Ohkoshi, Effect of Aprotinin on Growth of 3-Methylcholanthrene-Induced Squamous Cell Carcinoma In Mice, Gann 71: 246-250 (1980).

Troll et al., Protease Inhibitors as Anticarcinogens, JNCL 73(6): 1245-1250 (1984).

Emori et al., All Four Repeating Domains of the Endogenous Inhibitor for Calcium-dependent Protease Independently Retain Inhibitory Activity, Journal of Biological Chemistry 263(5): 2364-2370 (1988).

Witschi et al., Modulation of lung tumor development in mice with the soybean-derived Bowman-Birk protease inhibitor, Carcinogenesis 10:2275-2277 (1989).

Orkin et al., Report & Recommendations of the Panel to Assess the NIH Investment in Research on Gene Therapy, NIH (1995).

Carillo et al., Differential sensitivity of FOS and JUN family members to calpains, Oncogene 9, 1679-1689 (1994).

Y. Emori et al. All Four Repeating Domains of the Endogenous Inhibitor for Calcium-dependent Protease Independently Retain Inhibitory Activity, J. Biol Chem 263:2364-2370;1988.

H. Witschi et al. Modulation of lung tumor development in mice with the soybean-derived Bowman-Birk protease inhibitor, Carcinogenesis 10:2275-2277 (1989).

W. Trolli et al. Protease Inhibitors as Anticarcinogens, JNCI 73 (6):1245-1250, date=1984 ; author=Troll.

M. Ohkoshi (1980) Gann 71: 246-250.

Carillo et al., "Differential sensitivity of FOS and JUN family members to calpains", Oncogene 9, 1679-1689 (1994).

Levrero et al., "Defective and Nondefective Adenovirus Vectors for Expression Foreign Genes in Vitro and In Vivo", Gene, 101, 195-202, (1991).

Maki et al., "Inhibition of Calpain by a Synthetic Oligopeptide Corresponding to an Exon of the Human Calpastain Gene" Journal of Biol. Chemistry, 254, (32), 18866-18869 1989.

Ohkoshi, "Effect of Aprotinin on Growth of 3-Methylcholanthrene-Induced Squamous Cell Carcinoma in Mice", Gann 71: 246-250 (1980).

Orkin, et al., "Report & Recommendations of the Panel to Assess the NIH Investment in Research on Gene Therapy", NIH, 1-20 (Dec. 1995).

Dach, et al. "Targeting gene therapy to cancer: A Review", Oncology rES., vol. 9: 313-325, 1997.

Verma et al., "Gene therapy—promises, problems and prospects", Nature, vol. 389: 239-242 (Sep. 1997).

Eck et al., "Gene-based therapy", Goodman & Gilman's The Pharmacological Basis of Therapeutics, McGraw-Hill Nith Edition: 77-101. (1996).

Asada et al., "cDNA cloning of human calpastain; sequence homology among human, pig, and rabbit calpastatins" J. Enzym. Inhib., vol. 3(1): 49-56 (1989).

Bischoff et al., "An adenovirus mutant that replicates selectively in p53-deficient human tumor cells." Science, vol. 274:373-376. (Oct. 1996.

Miller et al., "Target vectors for gene therapy", FASEB, vol. 9: 190-199 (Feb. 1995).

Crystal, RG., "Transfer of Genes to Humans: Early lessons and obstacles to success", Science, vol. 270: 404-410. (1995).

Marshall, "Gene Therapy's Growing Pains", Science, vol. 269:1050-1055 (1995).

Anderson, W. French, Nature Medicine, vol. 6 No. 8, p. 862 (Aug. 2000).

Wagenknecht, et al., "Proteasome Inhibitors Induces p53/p21-Independent Apoptosis in Human Giloma Cells", Cell Physiol Biochem (1999); 9:117-125.

An, et al., "Protease inhibitor-induced apoptosis: accumulation of wp p53, p51 WAF1/CIP1, and induction of apoptosis are independent . . . ", Luekemia (2000) 14:1276-1283.

Kubbutat, et al., "Proteolytic Cleavage of Human p53 by Calpain: a Potential Regulator of protein Stability", Molecular and Cellular Biology, (Jan. 1997); pp. 46-468.

Kubbutat, et al., "Keeping an old friend under control: regulation of p53 stability", Molecular Medicine Today (Jun. 1998): pp. 250-256.

Atencio, et al., "Celpain Inhibitor 1 Activates p53-dependent Apoptosis in Tumor Cell Lines", Cell Growth & Differentiation, 5/200: vol. 11, pp. 247-253.

Pariat, et al., "Proteolysis by Calpains: a Possible Contribution to Degradation of p53", Molecular and Cellular Biology, (May 1997): vol. 17(5): pp. 2806-2815.

Carafoli, et al., "Breakthroughs and Views Calpain: A Protease in Search of a Function?", Biochemical and Biophysical Research Communications 247:193-203 (1998).

* cited by examiner

SEQUENCE LISTING

<160> NUMBER OF SEQ ID NOS: 4

<210> SEQ ID NO 1
<211> LENGTH: 2085
<212> TYPE: DNA
<213> ORGANISM: Homo sapiens
<220> FEATURE:
<221> NAME/KEY: CDS
<222> LOCATION: (1)..(2085)

<400> SEQUENCE: 1

```
atg gaa gga cca cat ctt cct aac aag aaa aaa cac aaa aaa cag gct      48
Met Glu Gly Pro His Leu Pro Asn Lys Lys Lys His Lys Lys Gln Ala
 1               5                  10                  15
```

-continued

| | | |
|---|---|---|
| gta aaa aca gaa cct gag aag aag tca cag tca acc aag ctg tct gtg<br>Val Lys Thr Glu Pro Glu Lys Lys Ser Gln Ser Thr Lys Leu Ser Val<br>20                        25                    30 | 96 |
| gtt cat gag aaa aaa tcc caa gaa gga aag cca aaa gaa cac aca gag<br>Val His Glu Lys Lys Ser Gln Glu Gly Lys Pro Lys Glu His Thr Glu<br>    35                      40                    45 | 144 |
| cca aaa agc cta ccc aag cag gca tca gat aca gga agt aac gat gct<br>Pro Lys Ser Leu Pro Lys Gln Ala Ser Asp Thr Gly Ser Asn Asp Ala<br>50                        55                    60 | 192 |
| cac aat aaa aaa gca gtt tcc aga tca gct gaa cag cag cca tca gag<br>His Asn Lys Lys Ala Val Ser Arg Ser Ala Glu Gln Gln Pro Ser Glu<br>65                        70                    75                    80 | 240 |
| aaa tca aca gaa cca aag act aaa cca caa gac atg att tct gct ggt<br>Lys Ser Thr Glu Pro Lys Thr Lys Pro Gln Asp Met Ile Ser Ala Gly<br>                  85                      90                    95 | 288 |
| gga gag agt gtt gct ggt atc act gca ata tct ggc aag ccg ggt gac<br>Gly Glu Ser Val Ala Gly Ile Thr Ala Ile Ser Gly Lys Pro Gly Asp<br>100                      105                    110 | 336 |
| aag aaa aaa gaa aag aaa tca tta acc cca gct gtg cca gtt gaa tct<br>Lys Lys Lys Glu Lys Lys Ser Leu Thr Pro Ala Val Pro Val Glu Ser<br>115                      120                    125 | 384 |
| aaa ccg gat aaa cca tcg gga aag tca ggc atg gat gct gct ttg gat<br>Lys Pro Asp Lys Pro Ser Gly Lys Ser Gly Met Asp Ala Ala Leu Asp<br>130                      135                    140 | 432 |
| gac tta ata gat act tta gga gga cct gaa gaa act gaa gaa gaa aat<br>Asp Leu Ile Asp Thr Leu Gly Gly Pro Glu Glu Thr Glu Glu Glu Asn<br>145                      150                    155                    160 | 480 |
| aca acg tat act gga cca gaa gtt tca gat cca atg agt tcc acc tac<br>Thr Thr Tyr Thr Gly Pro Glu Val Ser Asp Pro Met Ser Ser Thr Tyr<br>                  165                    170                    175 | 528 |
| ata gag gaa ttg ggt aaa aga gaa gtc aca att cct cca aaa tat agg<br>Ile Glu Glu Leu Gly Lys Arg Glu Val Thr Ile Pro Pro Lys Tyr Arg<br>180                      185                    190 | 576 |
| gaa cta ttg gct aaa aag gaa ggg atc aca ggg cct cct gca gac tct<br>Glu Leu Leu Ala Lys Lys Glu Gly Ile Thr Gly Pro Pro Ala Asp Ser<br>195                      200                    205 | 624 |
| tca aaa ccc ata ggg cca gat gat gct ata gac gcc ttg tca tct gac<br>Ser Lys Pro Ile Gly Pro Asp Asp Ala Ile Asp Ala Leu Ser Ser Asp<br>210                      215                    220 | 672 |
| ttc acc tgt ggg tcg cct aca gct gct gga aag aaa act gaa aaa gag<br>Phe Thr Cys Gly Ser Pro Thr Ala Ala Gly Lys Lys Thr Glu Lys Glu<br>225                      230                    235                    240 | 720 |
| gaa tct aca gaa gtt tta aaa gct cag tca gca ggg aca gtc aga agt<br>Glu Ser Thr Glu Val Leu Lys Ala Gln Ser Ala Gly Thr Val Arg Ser<br>                  245                    250                    255 | 768 |
| gct gct cca ccc caa gag aag aaa aga aag gtg gag aag gat aca atg<br>Ala Ala Pro Pro Gln Glu Lys Lys Arg Lys Val Glu Lys Asp Thr Met<br>260                      265                    270 | 816 |
| agt gat caa gca ctc gag gct ctg tcg gct tca ctg ggc acc cgg caa<br>Ser Asp Gln Ala Leu Glu Ala Leu Ser Ala Ser Leu Gly Thr Arg Gln<br>275                      280                    285 | 864 |
| gca gaa cct gag ctc gac ctc cgc tca att aag gaa gtc gat gag gca<br>Ala Glu Pro Glu Leu Asp Leu Arg Ser Ile Lys Glu Val Asp Glu Ala<br>290                      295                    300 | 912 |
| aaa gct aaa gaa gaa aaa cta gag aag tgt ggt gag gat gaa aca<br>Lys Ala Lys Glu Glu Lys Leu Glu Lys Cys Gly Glu Asp Asp Glu Thr<br>305                      310                    315                    320 | 960 |
| atc cca tct gag tac aga tta aaa cca gcc acg gat aaa gat gga aaa<br>Ile Pro Ser Glu Tyr Arg Leu Lys Pro Ala Thr Asp Lys Asp Gly Lys | 1008 |

-continued

```
                  325                 330                 335
cca cta ttg cca gag cct gaa gaa aaa ccc aag cct cgg agt gaa tca     1056
Pro Leu Leu Pro Glu Pro Glu Glu Lys Pro Lys Pro Arg Ser Glu Ser
            340                 345                 350 gaa ctc att gat gaa ctt tca gaa gat ttt gac cgg tct gaa tgt aaa     1104
Glu Leu Ile Asp Glu Leu Ser Glu Asp Phe Asp Arg Ser Glu Cys Lys
                355                 360                 365 gag aaa cca tct aag cca act gaa aag aca gaa gaa tct aag gcc gct     1152
Glu Lys Pro Ser Lys Pro Thr Glu Lys Thr Glu Glu Ser Lys Ala Ala
        370                 375                 380 gct cca gct cct gtg tcg gag gct gtg tct cgg acc tcc atg tgt agt     1200
Ala Pro Ala Pro Val Ser Glu Ala Val Ser Arg Thr Ser Met Cys Ser
385                 390                 395                 400 ata cag tca gca ccc cct gag ccg gct acc ttg aag ggc aca gtg cca     1248
Ile Gln Ser Ala Pro Pro Glu Pro Ala Thr Leu Lys Gly Thr Val Pro
                405                 410                 415 gat gat gct gta gaa gcc ttg gct gat agc ctg ggg aaa aag gaa gca     1296
Asp Asp Ala Val Glu Ala Leu Ala Asp Ser Leu Gly Lys Lys Glu Ala
            420                 425                 430 gat cca gaa gat gga aaa cct gtg atg gat aaa gtc aag gag aag gcc     1344
Asp Pro Glu Asp Gly Lys Pro Val Met Asp Lys Val Lys Glu Lys Ala
        435                 440                 445 aaa gaa gaa gac cgt gaa aag ctt ggt gaa aaa gaa gaa aca att cct     1392
Lys Glu Glu Asp Arg Glu Lys Leu Gly Glu Lys Glu Glu Thr Ile Pro
450                 455                 460 cct gat tat aga tta gaa gag gtc aag gat aaa gat gga aag cca ctc     1440
Pro Asp Tyr Arg Leu Glu Glu Val Lys Asp Lys Asp Gly Lys Pro Leu
465                 470                 475                 480 ctg cca aaa gag tct aag gaa cag ctt cca ccc atg agt gaa gac ttc     1488
Leu Pro Lys Glu Ser Lys Glu Gln Leu Pro Pro Met Ser Glu Asp Phe
                485                 490                 495 ctt ctg gat gct ttg tct gag gac ttc tct ggt cca caa aat gct tca     1536
Leu Leu Asp Ala Leu Ser Glu Asp Phe Ser Gly Pro Gln Asn Ala Ser
            500                 505                 510 tct ctt aaa ttt gaa gat gct aaa ctt gct gct gcc atc tct gaa gtg     1584
Ser Leu Lys Phe Glu Asp Ala Lys Leu Ala Ala Ala Ile Ser Glu Val
        515                 520                 525 gtt tcc caa acc cca gct tca acg acc caa gct gga gcc cca ccc cgt     1632
Val Ser Gln Thr Pro Ala Ser Thr Thr Gln Ala Gly Ala Pro Pro Arg
530                 535                 540 gat acc tcg cag agt gac aaa gac ctc gat gat gcc ttg gat aaa ctc     1680
Asp Thr Ser Gln Ser Asp Lys Asp Leu Asp Asp Ala Leu Asp Lys Leu
545                 550                 555                 560 tct gac agt cta gga caa agg cag cct gac cca gat gag aac aaa cca     1728
Ser Asp Ser Leu Gly Gln Arg Gln Pro Asp Pro Asp Glu Asn Lys Pro
                565                 570                 575 atg gga gat aaa gta aag gaa aaa gct aaa gct gaa cat aga gac aag     1776
Met Gly Asp Lys Val Lys Glu Lys Ala Lys Ala Glu His Arg Asp Lys
            580                 585                 590 ctt gga gaa aga gat gac act atc cca cct gaa tac aga cat ctc ctg     1824
Leu Gly Glu Arg Asp Asp Thr Ile Pro Pro Glu Tyr Arg His Leu Leu
        595                 600                 605 gat gat aat gga cag gac aaa cca gtg aag cca cct aca aag aaa tca     1872
Asp Asp Asn Gly Gln Asp Lys Pro Val Lys Pro Pro Thr Lys Lys Ser
610                 615                 620 gag gat tca aag aaa cct gca gat gac caa gac ccc att gat gct ctc     1920
Glu Asp Ser Lys Lys Pro Ala Asp Asp Gln Asp Pro Ile Asp Ala Leu
625                 630                 635                 640 tca gga gat ctg gac agc tgt ccc tcc act aca gaa acc tca cag aac     1968
```

```
Ser Gly Asp Leu Asp Ser Cys Pro Ser Thr Thr Glu Thr Ser Gln Asn
            645                 650                 655 aca gca aag gat aag tgc aag aag gct gct tcc agc tcc aaa gca cct      2016
Thr Ala Lys Asp Lys Cys Lys Lys Ala Ala Ser Ser Ser Lys Ala Pro
            660                 665                 670 aag aat gga ggt aaa gcg aag gat tca gca aag aca aca gag gaa act      2064
Lys Asn Gly Gly Lys Ala Lys Asp Ser Ala Lys Thr Thr Glu Glu Thr
            675                 680                 685 tcc aag cca aaa gat gac taa                                           2085
Ser Lys Pro Lys Asp Asp
            690         695

<210> SEQ ID NO 2
<211> LENGTH: 694
<212> TYPE: PRT
<213> ORGANISM: Homo sapiens

<400> SEQUENCE: 2

Met Glu Gly Pro His Leu Pro Asn Lys Lys His Lys Lys Gln Ala
 1               5                  10                  15

Val Lys Thr Glu Pro Glu Lys Lys Ser Gln Ser Thr Lys Leu Ser Val
            20                  25                  30

Val His Glu Lys Lys Ser Gln Glu Gly Lys Pro Lys Glu His Thr Glu
        35                  40                  45

Pro Lys Ser Leu Pro Lys Gln Ala Ser Asp Thr Gly Ser Asn Asp Ala
    50                  55                  60

His Asn Lys Lys Ala Val Ser Arg Ser Ala Glu Gln Pro Ser Glu
 65                 70                  75                  80

Lys Ser Thr Glu Pro Lys Thr Lys Pro Gln Asp Met Ile Ser Ala Gly
                85                  90                  95

Gly Glu Ser Val Ala Gly Ile Thr Ala Ile Ser Gly Lys Pro Gly Asp
            100                 105                 110

Lys Lys Lys Glu Lys Lys Ser Leu Thr Pro Ala Val Pro Val Glu Ser
        115                 120                 125

Lys Pro Asp Lys Pro Ser Gly Lys Ser Gly Met Asp Ala Ala Leu Asp
    130                 135                 140

Asp Leu Ile Asp Thr Leu Gly Gly Pro Glu Glu Thr Glu Glu Glu Asn
145                 150                 155                 160

Thr Thr Tyr Thr Gly Pro Glu Val Ser Asp Pro Met Ser Ser Thr Tyr
                165                 170                 175

Ile Glu Glu Leu Gly Lys Arg Glu Val Thr Ile Pro Pro Lys Tyr Arg
            180                 185                 190

Glu Leu Leu Ala Lys Lys Glu Gly Ile Thr Gly Pro Pro Ala Asp Ser
        195                 200                 205

Ser Lys Pro Ile Gly Pro Asp Asp Ala Ile Asp Ala Leu Ser Ser Asp
    210                 215                 220

Phe Thr Cys Gly Ser Pro Thr Ala Ala Gly Lys Lys Thr Glu Lys Glu
225                 230                 235                 240

Glu Ser Thr Glu Val Leu Lys Ala Gln Ser Ala Gly Thr Val Arg Ser
                245                 250                 255

Ala Ala Pro Pro Gln Glu Lys Lys Arg Lys Val Glu Lys Asp Thr Met
            260                 265                 270

Ser Asp Gln Ala Leu Glu Ala Leu Ser Ala Ser Leu Gly Thr Arg Gln
        275                 280                 285

Ala Glu Pro Glu Leu Asp Leu Arg Ser Ile Lys Glu Val Asp Glu Ala
    290                 295                 300
```

Lys Ala Lys Glu Glu Lys Leu Glu Lys Cys Gly Glu Asp Asp Glu Thr
305                 310                 315                 320

Ile Pro Ser Glu Tyr Arg Leu Lys Pro Ala Thr Asp Lys Asp Gly Lys
            325                 330                 335

Pro Leu Leu Pro Glu Pro Glu Lys Pro Lys Pro Arg Ser Glu Ser
            340                 345                 350

Glu Leu Ile Asp Glu Leu Ser Glu Asp Phe Asp Arg Ser Glu Cys Lys
            355                 360                 365

Glu Lys Pro Ser Lys Pro Thr Glu Lys Thr Glu Glu Ser Lys Ala Ala
    370                 375                 380

Ala Pro Ala Pro Val Ser Glu Ala Val Ser Arg Thr Ser Met Cys Ser
385                 390                 395                 400

Ile Gln Ser Ala Pro Glu Pro Ala Thr Leu Lys Gly Thr Val Pro
                405                 410                 415

Asp Asp Ala Val Glu Ala Leu Ala Asp Ser Leu Gly Lys Lys Glu Ala
            420                 425                 430

Asp Pro Glu Asp Gly Lys Pro Val Met Asp Lys Val Lys Glu Lys Ala
        435                 440                 445

Lys Glu Glu Asp Arg Glu Lys Leu Gly Glu Lys Glu Glu Thr Ile Pro
    450                 455                 460

Pro Asp Tyr Arg Leu Glu Glu Val Lys Asp Lys Asp Gly Lys Pro Leu
465                 470                 475                 480

Leu Pro Lys Glu Ser Lys Glu Gln Leu Pro Pro Met Ser Glu Asp Phe
            485                 490                 495

Leu Leu Asp Ala Leu Ser Glu Asp Phe Ser Gly Pro Gln Asn Ala Ser
            500                 505                 510

Ser Leu Lys Phe Glu Asp Ala Lys Leu Ala Ala Ala Ile Ser Glu Val
        515                 520                 525

Val Ser Gln Thr Pro Ala Ser Thr Thr Gln Ala Gly Ala Pro Pro Arg
    530                 535                 540

Asp Thr Ser Gln Ser Asp Lys Asp Leu Asp Ala Leu Asp Lys Leu
545                 550                 555                 560

Ser Asp Ser Leu Gly Gln Arg Gln Pro Asp Pro Asp Glu Asn Lys Pro
            565                 570                 575

Met Gly Asp Lys Val Lys Glu Lys Ala Lys Ala Glu His Arg Asp Lys
            580                 585                 590

Leu Gly Glu Arg Asp Asp Thr Ile Pro Pro Glu Tyr Arg His Leu Leu
        595                 600                 605

Asp Asp Asn Gly Gln Asp Lys Pro Val Lys Pro Pro Thr Lys Lys Ser
    610                 615                 620

Glu Asp Ser Lys Lys Pro Ala Asp Asp Gln Asp Pro Ile Asp Ala Leu
625                 630                 635                 640

Ser Gly Asp Leu Asp Ser Cys Pro Ser Thr Thr Glu Thr Ser Gln Asn
            645                 650                 655

Thr Ala Lys Asp Lys Cys Lys Lys Ala Ala Ser Ser Ser Lys Ala Pro
            660                 665                 670

Lys Asn Gly Gly Lys Ala Lys Asp Ser Ala Lys Thr Thr Glu Glu Thr
        675                 680                 685

Ser Lys Pro Lys Asp Asp
    690

<210> SEQ ID NO 3
<211> LENGTH: 399

```
<212> TYPE: DNA
<213> ORGANISM: Homo sapiens
<220> FEATURE:
<221> NAME/KEY: CDS
<222> LOCATION: (1)..(399)

<400> SEQUENCE: 3 tca ggc atg gat gct gct ttg gat gac tta ata gat act tta gga gga      48
Ser Gly Met Asp Ala Ala Leu Asp Asp Leu Ile Asp Thr Leu Gly Gly
 1               5                  10                  15 cct gaa gaa act gaa gaa gaa aat aca acg tat act gga cca gaa gtt      96
Pro Glu Glu Thr Glu Glu Glu Asn Thr Thr Tyr Thr Gly Pro Glu Val
            20                  25                  30 tca gat cca atg agt tcc acc tac ata gag gaa ttg ggt aaa aga gaa     144
Ser Asp Pro Met Ser Ser Thr Tyr Ile Glu Glu Leu Gly Lys Arg Glu
        35                  40                  45 gtc aca att cct cca aaa tat agg gaa cta ttg gct aaa aag gaa ggg     192
Val Thr Ile Pro Pro Lys Tyr Arg Glu Leu Leu Ala Lys Lys Glu Gly
 50                  55                  60 atc aca ggg cct cct gca gac tct tca aaa ccc ata ggg cca gat gat     240
Ile Thr Gly Pro Pro Ala Asp Ser Ser Lys Pro Ile Gly Pro Asp Asp
 65                  70                  75                  80 gct ata gac gcc ttg tca tct gac ttc acc tgt ggg tcg cct aca gct     288
Ala Ile Asp Ala Leu Ser Ser Asp Phe Thr Cys Gly Ser Pro Thr Ala
                85                  90                  95 gct gga aag aaa act gaa aaa gag gaa tct aca gaa gtt tta aaa gct     336
Ala Gly Lys Lys Thr Glu Lys Glu Glu Ser Thr Glu Val Leu Lys Ala
            100                 105                 110 cag tca gca ggg aca gtc aga agt gct gct cca ccc caa gag aag aaa     384
Gln Ser Ala Gly Thr Val Arg Ser Ala Ala Pro Pro Gln Glu Lys Lys
        115                 120                 125 aga aag gtg gag aag                                                  399
Arg Lys Val Glu Lys
    130

<210> SEQ ID NO 4
<211> LENGTH: 133
<212> TYPE: PRT
<213> ORGANISM: Homo sapiens

<400> SEQUENCE: 4

Ser Gly Met Asp Ala Ala Leu Asp Asp Leu Ile Asp Thr Leu Gly Gly
 1               5                  10                  15

Pro Glu Glu Thr Glu Glu Glu Asn Thr Thr Tyr Thr Gly Pro Glu Val
            20                  25                  30

Ser Asp Pro Met Ser Ser Thr Tyr Ile Glu Glu Leu Gly Lys Arg Glu
        35                  40                  45

Val Thr Ile Pro Pro Lys Tyr Arg Glu Leu Leu Ala Lys Lys Glu Gly
 50                  55                  60

Ile Thr Gly Pro Pro Ala Asp Ser Ser Lys Pro Ile Gly Pro Asp Asp
 65                  70                  75                  80

Ala Ile Asp Ala Leu Ser Ser Asp Phe Thr Cys Gly Ser Pro Thr Ala
                85                  90                  95

Ala Gly Lys Lys Thr Glu Lys Glu Glu Ser Thr Glu Val Leu Lys Ala
            100                 105                 110

Gln Ser Ala Gly Thr Val Arg Ser Ala Ala Pro Pro Gln Glu Lys Lys
        115                 120                 125

Arg Lys Val Glu Lys
    130
```

METHOD OF CANCER TREATMENT BY P53 PROTEIN CONTROL

The present invention relates to a new method for the treatment of cancer. More particularly, it relates to a method of treating cancer by regulating the cellular levels of the p53 protein. It also relates to vectors for gene therapy which make it possible to regulate the p53 protein, as well as the pharmaceutical compositions containing them.

For the past fifteen years, the molecular characterization of oncogenes and of tumour suppressor genes has made it possible to view the process of carcinogenesis in a new light. Thus, the increasingly detailed knowledge of the regulation of these genes and of the function of the corresponding proteins makes it possible to conceive new therapeutic approaches.

More particularly, the elucidation of the breakdown of the oncogenic and anti-oncogenic proteins represents a major challenge in terms of the fight against cancer since it presages, in the case of oncogenic proteins, the possibility of accelerating their degradation and therefore of annihilating their action, in the case of tumour suppressors, inhibiting their degradation and therefore increasing their antiproliferative or anti-tumour effect, in the case or mutated proteins, potentiating their antigenic presentation by molecules of the Major Histocompatibility Complex and thereby stimulating a tumour-specific immune response, and, in the case where the high expression of the oncogene or of the anti-oncogene is capable of inducing programmed cell death, the possibility of stabilizing these proteins so as to trigger the apoptotic process.

Originally, the p53 protein was classified as a nuclear oncogene since it could, in transfection experiments, extend the life of rodent cells in culture as well as cooperate with activated oncogenes such as ras to transform cells in primary culture. Indeed, the genes used in these first experiments were mutated and led to the expression of variant p53 proteins characterized by a gain in function. Without excluding functions which might still be discovered, it is now known that the p53 protein, at least in its wild-type form, is a transcription factor which negatively regulates growth and cell division and which, in certain situations, is capable of inducing apoptosis (Yonish-Rouach et al., Nature, 352, 345-347, 1991). Given that these properties manifest themselves in a stress situation where the integrity of the cellular DNA is threatened, it has been suggested that p53 is a "guardian of the genome". The presence of mutated p53 proteins in about 40% of human tumours, all types taken together, reinforces this hypothesis and underlines the probably critical role which mutations of this gene play in the tumour development (for reviews, see Montenarh, Oncogene, 7, 1673-1680, 1992; Oren, FASEB J., 6, 3169-3176, 1992; Zambetti and Levine, FASEB J., 7, 855-865, 1993).

The wild-type p53 protein is subject to a complex regulation which involves the control of its synthesis and of its breakdown as well as that of its intracellular location and of its post translational modifications (see the reviews cited above). The wild-type p53 protein is extremely unstable with a half-life of a few minutes. In contrast, some mutated proteins which accumulate at a high level in tumours have a significantly extended half-life. Little has been clearly established as regards the degradation of p53. Indeed, neither the intracellular sites of degradation, nor the number and the nature of the catabolic pathways taken, nor the peptide units labelling p53 for its degradation are known. To our knowledge, the only information available relates to the involvement of the enzyme E1 of the ubiquitin cycle under certain experimental conditions (Ciechanover et al., Proc. Natl. Acad. Sci. USA 88, 139-143, 1991; Chowdary et al., Molec. Cell. Biol. 14, 1997-2003, 1994). Moreover, it has been shown that certain proteolytic products derived from p53 may be presented in an antigenic manner.

The present invention results partly from the demonstration that the p53 proteins are substrates for calcium-dependent proteases: the calpains. It results more particularly from the demonstration that the p53 proteins are degraded specifically by m-calpain or μ-calpain. The present invention constitutes the first demonstration of a mechanism for regulating the cellular levels of the p53 proteins and thus offers a new particularly effective and specific approach for modulating the levels of this protein in pathological situations such as especially certain cancers.

In particular, the present invention describes a new approach for the treatment of cancer, based on the use of compounds which modulate the activity of calpains on the p53 proteins, which make it possible either to activate the degradation of the mutated p53 proteins, in order to block their tumorigenic effect and/or to enhance the presentation of immunogenic peptides, or to stabilize the wild-type p53 protein, in order to counterbalance the tumorigenic effect of the mutated proteins expressed in the tumours and/or in order to induce the apoptosis of the tumour cells.

A first subject of the invention therefore consists in the use of a compound capable of modulating the activity of calpain for the preparation of a pharmaceutical composition for the treatment of cancers.

Calpains are ubiquitous enzymes found in most mammalian cells (for a review, see Croall and deMartino, Physiol. Rev., 71, 813-847, 1991). They are essentially cytoplasmic but they can penetrate into the nucleus by virtue of the destruction of the nuclear envelope during mitosis or following certain stimuli. As indicated above, the proteolytic activity of calpains is dependent on the presence of calcium.

The compounds capable of modulating the activity of calpain for the purposes of the present invention may be of several types.

They may be compounds capable of inhibiting the activity of the calpain on the p53 proteins. These compounds are particularly advantageous since they can be used to inhibit, at least in part, the degradation of the wild-type p53 protein. These compounds therefore make it possible to stabilize intracellularly the wild-type p53 protein and to counterbalance the effect of the mutated forms. Among the inhibitory compounds which can be used within the framework of the invention there may be mentioned the protease inhibitors (leupeptin, aprotinin, PMSF, and the like), the calcium chelators (EGTA, EDTA, and the like) or more specific inhibitors such as calpastatin or any fragment or derivative thereof. Calpastatin is a known inhibitor of the calpains. Its sequence has been described in the prior art (SEQ ID No. 1). A particularly advantageous embodiment of the present invention consists in transferring into the tumours a vector carrying all or part of the sequence encoding calpastatin. This approach is particularly adapted to the treatment of cancers which always have a wild-type p53 allele, such as colic or bronchial carcinomas for example. Various fragments or derivatives of calpastatin can be used within the framework of the present invention. Such fragments or derivatives may be any molecule obtained from the sequence SEQ ID No. 1 by modification(s) of a genetic and/or chemical nature, preserving the capacity to inhibit, at least in part, the activity of a calpain. Modification of a genetic and/or chemical nature is understood to mean any mutation, deletion, substitution, addition and/or modification of one or more nucleotides. Such modifications may be carried out with various ends, especially that of preparing sequences adapted to expression in a specific type of vector or host, that of reducing the size of the sequence so as to facilitate their cellular penetration, that of increasing the inhibitory activity, or, in a particularly advantageous manner, of increasing the selectivity of the inhibitor towards the activity of the calpains on the degradation of the wild-type p53 protein.

Such modifications may be carried out, for example, by in vitro mutagenesis, by introduction of additional constituents or of synthetic sequences, or by deletions or substitutions of the original constituents. When a derivative as defined above is prepared, its activity as inhibitor of the activity of the calpains on p53 proteins can be demonstrated in several ways, and in particular by bringing into contact the said inhibitor and the various forms of p53 proteins, and then by detecting the degradation products obtained (see Examples 1 to 3). Any other technique known to persons skilled in the art can obviously be used to this effect.

In a specific embodiment of the present invention, all or part of calpastatin, or a nucleic acid encoding all or part of calpastatin is used as inhibitor. Still more particularly, a peptide comprising all or part of the sequence SEQ ID No. 1 or of a derivative thereof is used.

As regards more particularly the derivatives, there may be mentioned, by way of example, the compound of sequence SEQ ID No. 2, which corresponds to a fragment of calpastatin. There is advantageously used any derivative composed of the sequence SEQ ID No. 1 or 2 which is capable of specifically or preferentially inhibiting the degradation of the wild-type p53 protein by calpain.

The compounds capable of modulating the activity of calpain on the p53 proteins for the purposes of the present invention may also be derivative of calpain capable of specifically or preferentially degrading the mutated p53 proteins. Such derivatives are also very advantageous since they make it possible to activate the degradation of the mutated p53 proteins, in order to block their tumorigenic effect and/or to increase the presentation of the immunogenic peptides, without significantly affecting the cellular levels of the wild-type p53 protein. Such derivatives may be obtained from calpain, by structural modification(s) of a genetic and/or chemical nature. The capacity of the derivatives thus obtained to specifically or preferentially degrade the mutated p53 proteins may then be demonstrated as described in Examples 1 to 3.

Preferably, the modulators used within the framework of the invention are proteins or polypeptides, or nucleic acid sequences encoding these polypeptides or proteins. Still more preferably, the modulatory compounds are proteins or polypeptides which are specific inhibitors of the activity of calpain on the wild-type p53 protein or forms of calpains, modified or otherwise, for specifically degrading the mutated p53 proteins.

In a particularly advantageous manner, the invention consists in the possibility of bringing about the expression in cancer cells having both a wild-type p53 allele and a mutated p53 allele of nucleic sequences encoding inhibitors of calpain, such as calpastatin or part of calpastatin, or forms of calpains, modified or otherwise, for specifically degrading the mutated p53 proteins.

The nucleic acid sequence used within the framework of the present invention may be administered as such, in the form of naked DNA according to the technique described in Application WO 90/11092. It can also be administered in a form complexed, for example, with DEAE-dextran (Pagano et al., J. Virol. 1 (1967) 891), with nuclear proteins (Kaneda et al., Science 243 (1989) 375), with lipids (Felgner et al., PNAS 84 (1987) 7413), in the form of liposomes (Fraley et al., J. Biol. Chem. 255 (1980) 10431), and the like. Preferably, the sequence used within the framework of the invention forms part of a vector. The use of such a vector indeed makes it possible to improve the administration of the nucleic acid into the cells to be treated, and also to increase its stability in the said cells, which makes it possible to obtain a lasting therapeutic effect. Furthermore, it is possible to introduce several nucleic acid sequences into the same vector, which also increases the efficacy of the treatment.

The vector used may be of various origin, as long as it is capable of transforming animal cells, preferably human cancer cells. In a preferred embodiment of the invention, a viral vector is used which may be chosen from adenoviruses, retroviruses, adeno-associated viruses (AAV) or the herpes virus.

In this regard, the subject of the present invention is any recombinant virus comprising, inserted into its genome, a nucleic acid encoding a compound capable of modulating the activity of calpain. Preferably, the viruses used within the framework of the invention are defective, that is to say that they are incapable of replicating autonomously in the infected cell. Generally, the genome of the defective viruses used within the framework of the present invention therefore lacks at least the sequences necessary for the replication of the said virus in the infected cell. These regions may be either removed (completely or in part), or made nonfunctional, or substituted by other sequences and especially by the sequence encoding the modulator of the calpains. Preferably, the defective virus retains, nevertheless, the sequences of its genome which are necessary for the encapsidation of the viral particles.

As regards more particularly adenoviruses, various serotypes, whose structure and properties vary somewhat, have been characterized. Among these serotypes, the use of the type 2 or 5 human adenoviruses (Ad 2 or Ad 5) or of the adenoviruses of animal origin (see application FR 93 05954) is preferred within the framework of the present invention. Among the adenoviruses of animal origin which can be used within the framework of the present invention, there may be mentioned adenoviruses of canine, bovine, murine (example: MVA1, Beard et al., Virology 75 (1990) 81), ovine, porcine, avian or alternatively simian (example: SAV) origin. Preferably, the adenovirus of animal origin is a canine adenovirus, or more preferably a CAV2 adenovirus [Manhattan strain or A26/61 (ATCC VR-800) for example]. Preferably, adenoviruses of human or canine or mixed origin are used within the framework of the invention.

Preferably, the defective adenoviruses of the invention comprise the ITRs, a sequence allowing the encapsidation and the sequence encoding the modulator of the calpains. Still more preferably, in the genome of the adenoviruses of the invention, the E1 gene and at least one of the genes E2, E4, L1-L5 are nonfunctional. The viral gene considered can be rendered non-functional by any technique known to persons skilled in the art, and especially by total suppression, by substitution or partial deletion, or by addition of one or more bases in the gene(s) considered. Such modifications can be obtained in vitro (on the isolated DNA) or in situ, for example by means of genetic engineering techniques, or alternatively by treating with mutagenic agents.

The defective recombinant adenoviruses according to the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the DNA sequence encoding the modulator of the calpains. The homologous recombination occurs after co-transfection of the said adenoviruses and plasmid into an appropriate cell line. The cell line used should preferably (i) be transformable by the said elements, and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated in its genome, the left hand part of the genome of an Ad5 adenovirus (12%). Strategies for constructing vectors derived from adenoviruses have also been described in Applications Nos. FR 93 05954 and FR 93 08596.

Next, the adenoviruses which have multiplied are recovered and purified according to conventional molecular biology techniques as illustrated in the examples.

As regards the adeno-associated viruses (AAV), they are relatively small DNA viruses which become integrated into the genome of the cells which they infect, in a stable and site-specific manner. They are capable of infecting a broad spectrum of cells, without inducing any effect on cell growth, morphology or differentiation. Moreover, they do not seem to be involved in pathologies in man. The genome of the AAVs has been cloned, sequenced and characterized. It comprises about 4700 bases and contains, at each end, an inverted repeat region (ITR) of about 145 bases which serves as replication origin for the virus. The remainder of the genome is divided into 2 essential regions carrying the encapsidation functions: the left hand part of the genome, which contains the rep gene involved in the viral replication and the expression of the viral genes; the right hand part of the genome, which contains the cap gene encoding the virus capsid proteins.

The use of vectors derived from AAVs for the transfer of genes in vitro and in vivo has been described in the literature (see especially WO 91/18088; WO 93/09239; U.S. Pat. No. 4,797,368, U.S. Pat. No. 5,139,941, EP 488 528). These applications describe various constructs derived from AAVs, from which the rep and/or cap genes are deleted and replaced by a gene of interest, and their use for the transfer in vitro (on cells in culture) or in vivo (directly in an organism) of the said gene of interest. The defective recombinant AAVs according to the invention can be prepared by co-transfection, into a cell line infected by a human helper virus (for example an adenovirus), of a plasmid containing the sequence encoding the modulator of the calpains bordered by two AAV inverted repeat regions (ITR), and of a plasmid carrying the AAV encapsidation genes (rep and cap genes). The recombinant AAVs produced are then purified by conventional techniques.

As regards the herpes viruses and the retroviruses, the construction of recombinant vectors has been widely described in the literature: see especially Breakfield et al., New Biologist 3 (1991) 203; EP 453242, EP 178220, Bernstein et al. Genet. Eng. 7 (1985) 235; McCormick, BioTechnology 3 (1985) 689, and the like.

For carrying out the present invention, it is most particularly advantageous to use a defective recombinant retrovirus or adenovirus. These vectors indeed have particularly advantageous properties for the transfer of genes into tumour cells.

Advantageously, in the vectors of the invention, the sequence encoding the modulator of the calpains is placed under the control of signals allowing its expression in tumour cells. Preferably, these are heterologous expression signals, that is to say signals different from those which are naturally responsible for the expression of the modulator. They may be in particular sequences responsible for the expression of other proteins, or synthetic sequences. In particular, they may be promoter sequences of eukaryotic or viral genes. For example, they may be promoter sequences derived from the genome of the cell which it is desired to infect. Likewise, they may be promoter sequences derived from the genome of a virus, including the virus used. In this regard, the E1A, MLP, CMV, RSV-LTR promoters and the like may be mentioned for example. In addition, these expression sequences may be modified by addition of activating or regulatory sequences or of sequences allowing a tissue-specific expression. It may indeed be particularly advantageous to use expression signals which are active specifically or predominantly in tumour cells, so that the DNA sequence is expressed or produces its effect only when the virus has effectively infected a tumour cell.

In a specific embodiment, the invention relates to a defective recombinant virus comprising a cDNA sequence encoding a modulator of the calpains under the control of a viral promoter, preferably chosen from the RSV-LTR and the CMV promoter.

Still in a preferred embodiment, the invention relates to a defective recombinant virus comprising a DNA sequence encoding a modulator of the calpains under the control of a promoter allowing predominant expression in tumour cells.

The expression is considered to be predominant for the purposes of the invention when, even if a residual expression is observed in other cell types, the expression levels are greater in the tumour cells.

The present invention also relates to any pharmaceutical composition comprising one or more defective recombinant viruses as described above. These pharmaceutical compositions may be formulated for administrations via the topical, oral, parenteral, intranasal, intravenous, intramuscular, subcutaneous, intraocular or transdermal route and the like. Preferably, the pharmaceutical compositions of the invention contain a vehicle pharmaceutically acceptable for an injectable formulation, especially for a direct injection into the patient's tumour. This may be in particular isotonic sterile solutions, or dry, especially freeze-dried, compositions which, upon addition, depending on the case, of sterile water or of physiological saline, allow the preparation of injectable solutions. Direct injection into the patient's tumour is advantageous because it makes it possible to concentrate the therapeutic effect at the level of the affected tissues.

The doses of defective recombinant virus which are used for the injection may be adapted according to various parameters, and especially according to the viral vector, the mode of administration used, the relevant pathology or alternatively the desired duration of the treatment. In general, the recombinant adenoviruses according to the invention are formulated and administered in the form of doses of between $10^4$ to $10^{14}$ pfu/ml, and preferably $10^6$ to $10^{10}$ pfu/ml. The term pfu ("plaque forming unit") corresponds to the infectivity of a virus solution, and is determined by infecting an appropriate cell culture and measuring, generally after 48 hours, the number of plaques of infected cells. The techniques for determining the pfu titre of a viral solution are well documented in the literature. As regards the retroviruses, the compositions according to the invention may directly comprise the producing cells, for their implantation.

The present invention is particularly adapted to the treatment of cancers in which the mutated forms of p53 are observed. More specifically, the present invention is particularly advantageous for the treatment of cancers in which the wild-type and mutated alleles of p53 are present. Such cancers are especially colorectal cancer, breast cancer, lung cancer, gastric cancer, oesophageal cancer, B lymphomas, ovarian cancer, cancer of the bladder and the like.

The present invention will be more fully described with the aid of the following Examples which should be considered as illustrative and nonlimiting.

LEGEND TO THE FIGURES

FIG. 1: Study of the regulation of the p53 protein by calpain. The reaction is carried out in a final volume of 30 μl, of which 1 comes from the translation mixture. Line 1: T0; line 2: 30 min in the presence of 1 mM Calcium+20 μg/ml Calpain; line 4: 30 min in the presence of 1 mM Calcium+20 μg/ml Calpain+0.5 mg/ml calpastatin; line 5: 30 min in the presence of 1 mM Calcium+20 μg/ml Calpain+10=M EGTA; line 6: PBS; line 7: PBS+calcium; line 8: PBS+calpastatin.

GENERAL MOLECULAR BIOLOGY TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322 and pUC type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749-8764] using the kit distributed by Amersham.

The enzymatic amplification of the DNA fragments by the so-called PCR technique [Polymerase-catalyzed Chain Reaction, Saiki R. K. et al., Science 230 (1985) 1350-1354; Mullis K. B. and Faloona F. A., Meth. Enzym. 155 (1987) 335-350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463-5467] using the kit distributed by Amersham.

EXAMPLES

Example 1

This example shows that the addition of m-calpain to rabbit reticulocyte lysate induces the degradation of the wild-type p53 protein as well as that of certain mutated forms. This example also shows that inhibitors of calpains are capable of inhibiting the degradation of p53 and therefore of modulating the activity of this protein.

1.1. Demonstration of the degradation: mouse and human wild-type p53 proteins as well as various mutated p53 proteins (human proteins C273, H273, H175, I247) were translated in the rabbit reticulocyte lysate. The proteins thus obtained are resistant to any degradation, even in the presence of a high concentration of calcium (cofactor essential for the calpains). The addition of bovine m-calpain (Sigma) to the reticulocyte lysate in the presence of calcium led to the rapid disappearance of the neosynthesized proteins and the appearance of proteolytic fragments which are resolvable by electrophoresis. The degradation resistance of other proteins such as dihydrofolate reductase or glyceraldehyde-3-phosphate dehydrogenase under the same experimental conditions indicates the substrate specificity of the reaction.

1.2. Use of inhibitors of calpain for modulating the levels of p53 proteins: in the above Example 1.1., it was shown that the addition of m-calpain induced degradation of the p53 proteins. In this example, in addition to m-calpain, various compounds were introduced into the medium in order to test their capacity to inhibit the activity of calpain. The results obtained show that the addition of a calcium chelator (EGTA) as well as of a peptide which is a specific inhibitor of the calpains (derivative of a physiological inhibitor, calpastatin; Maki et al., J. Biol. Chem., 254, 18866-18869, 1989) are capable of inhibiting the degradation of the p53 proteins which is induced by the exogenous calpain.

Example 2

In the preceding example, it was shown that the addition of exogenous calpain to a solution of p53 proteins brought about their degradation. This example shows that the degradation of the wild-type p53 protein as well as that of certain mutated forms may be induced by the endogenous calpains in cytoplasmic extracts. This example also shows that inhibitors of the calpains are capable, in the presence of endogenous calpain, of inhibiting the degradation of p53 and therefore of modulating the activity of this protein.

2.1. Degradation by the endogenous calpains: mouse and human wild-type p53 proteins, as well as certain mutated forms (cf Example 1) were translated in the reticulocyte lysate and were then incubated in the presence of cytoplasmic extracts of Daudi or Jurkat human lymphoblastoid cells. The cytoplasmic extracts were prepared in the following manner: the cells (available at the ATCC) were cultured in DMEM medium supplemented with 10% foetal calf serum. The cells were then harvested, washed in PBS buffer and then incubated for 5 min in a detergent-free hypotonic lysis buffer (HEPES 20 mM, pH 7.5; KOAc 10 mM; MgOAc 1.5 mM; 2 ml per $5 \times 10^8$ cells). The lysis was completed using a Dounce homogenizer and then checked under a microscope. The nuclei were then removed by centrifugation at 2000 g for 5 min, and the supernatants were centrifuged at 10,000 g for 1 hour (Beckman SW60). The cytoplasmic extracts were then aliquoted in an amount of 5 to 12 mg/ml.

When the lysate of reticulocutes was incubated in the presence of cytoplasmic extracts, in the absence of calcium, no degradation was observed. On the other hand, in the presence of calcium, a very rapid degradation of the p53 proteins was observed, with the appearance of a characteristic proteolytic product profile similar to that obtained in Example 1. This experiment indeed shows that the p53 proteins are degraded by the endogenous calpains.

2.2. Use of calpain inhibitors to modulate the levels of p53 proteins: the chelation of calcium by EGTA, as well as the use of a whole range of protease inhibitors (leupeptin, aprotinin, soybean trypsin inhibitor and PMSF) and especially the peptide calpastatin show that the degradation of these proteins is dependent on the calpains of the cytoplasmic extract, and that various compounds capable of modulating the activity of the calpains may be used to regulate the p53 protein levels.

Example 3

This example demonstrates that the mouse and human wild-type p53 proteins are direct substrates for the calpains in the cytoplasmic extracts.

Figure 1A:
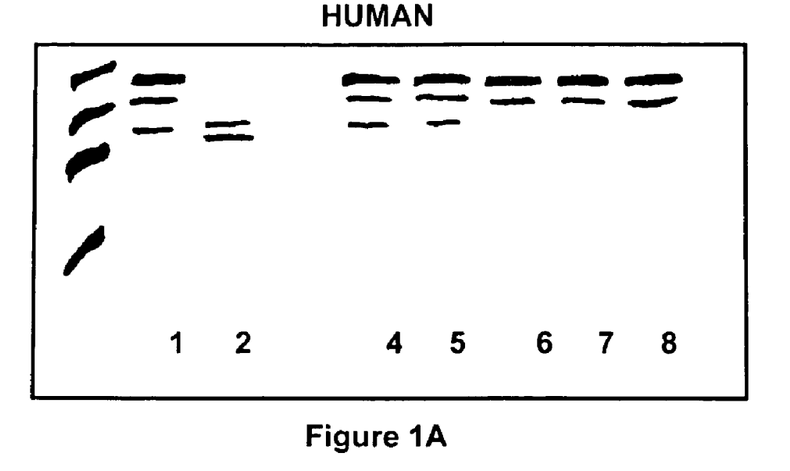
Figure 1B:
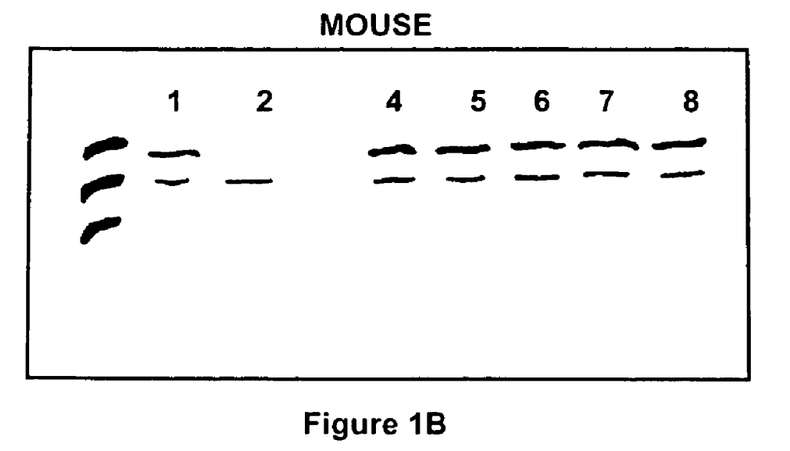

Examples 1 and 2 show that the calpains can induce the degradation of p53 in complex reaction mixtures. These experiments do not exclude, however, that under the conditions used, the calpains activate secondary proteases which are those which actually act on p53. In this example, the following experiment was conducted: (1) the mouse and human wild-type p53 proteins neosynthesized in the rabbit reticulocyte lysate were incubated for 30 minutes in the presence of a cytoplasmic extract of Daudi cells as well as in the presence of calcium to activate the calpains as in Example 2, (2) p53 protein was then added to the reaction mixture and the reaction was continued for 30 minutes under conditions permissive (same reaction conditions) or otherwise (addition either of EGTA to chelate the calcium, or of calpastatin peptide) for the calpains. In the presence of calcium, the newly added p53 protein is completely degraded, indicating that the protease activity is functional throughout the experiment. When the calpains are inhibited by the presence of EGTA or, more significantly, of the calpastatin peptide, the newly added p53 protein is, on the other hand, no longer degraded. This latter observation therefore excludes the possibility that in the first part of the experiment, the calpains induced a second protease responsible for the degradation of p53 (FIG. 1).

Example 4

This example describes the construction of a recombinant adenovirus comprising a nucleic acid sequence encoding calpastatin. This adenovirus is constructed by homologous recombination between the defective adenovirus Ad-dl1324 and a plasmid carrying the sequence SEQ ID No. 1 under the control of the RSV promoter.

4.1. Construction of the Plasmid SEQ ID No. 1

The plasmid SEQ ID No. 1 comprises the sequence encoding calpastatin under the control of the RSV-LTR promoter, as well as regions of the adenovirus which allow homologous recombination. It is constructed by inserting the sequence SEQ ID No. 1 into the plasmid pAd.RSVβgal. The plasmid pAd.RSVβGal contains, in the 5'→3' orientation, the PvuII fragment corresponding to the left hand end of the Ad5 adenovirus comprising: the ITR sequence, the replication origin, the encapsidation signals and the enhancer E1A;

the gene encoding β-galactosidase under the control of the RSV promoter (Rous sarcoma virus), a second fragment of the Ad5 adenovirus genome which allows homologous recombination between the plasmid pAd.RSVβGal and the adenovirus d1324. The plasmid pAd.RSVβGal has been described by Stratford-Perricaudet et al. (J. Clin. Invest. 90 (1992) 626).

4.2. Construction of the Recombinant Adenovirus

The vector described in 4.1. is linearized and cotransfected with a deficient adenoviral vector into the helper cells (line 293) providing in trans the functions encoded by the adenovirus E1 regions (E1A and E11B).

More specifically, the recombinant adenovirus is obtained by homologous recombination in vivo between the mutant adenovirus Ad-dl1324 (Thimmappaya et al., Cell 31 (1982) 543) and the vector described in Example 4.1., according to the following procedure: the plasmid SEQ ID No. 1 and the adenovirus Ad-dl1324, linearized by the enzyme ClaI, are cotransfected into the line 293 in the presence of calcium phosphate, so as to allow the homologous recombination. The recombinant adenoviruses thus generated are then selected by plaque purification. After isolation, the recombinant adenovirus DNA is amplified in the cell line 293, leading to a culture supernatant containing the unpurified recombinant defective adenovirus having a titre of about $10^{10}$ pfu/ml.

The viral particles are purified by centrifugation on a caesium chloride gradient according to known techniques (see especially Graham et al., Virology 52 (1973) 456). The adenovirus obtained may be stored at −80° C. in 20% glycerol.

The invention claimed is:

1. A method for detecting an inhibitor of p53 protein degradation comprising providing a cell extract containing one or more p53 protein and one or more proteases, administering a peptide or protein inhibitor of calpain protease activity of to the cell extract, and measuring p53 protein and p53 protein fragments, wherein the inhibitor administered is a calpastatin.

2. The method of claim 1, wherein the calpastatin is encoded by one of SEQ ID NO: 1-3.

3. The method of claim 1, wherein the cell extract is derived from a tumor cell.

4. The method of claim 1, wherein the inhibitor administered is a fragment of calpastatin.

5. The method of claim 3, wherein the inhibitor is a fragment of calpastatin.

6. The method of claim 1, wherein measuring the p53 protein and p53 protein fragments is performed using gel electrophoresis.

* * * * *